United States Patent [19]

Rowles

[11] Patent Number: 4,714,487
[45] Date of Patent: Dec. 22, 1987

[54] PROCESS FOR RECOVERY AND PURIFICATION OF $C_3$-$C_{4+}$ HYDROCARBONS USING SEGREGATED PHASE SEPARATION AND DEPHLEGMATION

[75] Inventor: Howard C. Rowles, Center Valley, Pa.

[73] Assignee: Air Products and Chemicals, Inc., Allentown, Pa.

[21] Appl. No.: 867,350

[22] Filed: May 23, 1986

[51] Int. Cl.[4] ............................................. F25J 3/02
[52] U.S. Cl. ............................................ 62/24; 62/32; 62/39; 62/44
[58] Field of Search ................... 62/11, 23, 24, 32, 38, 62/39, 42, 44

[56] References Cited

U.S. PATENT DOCUMENTS

| | | | |
|---|---|---|---|
| 3,635,038 | 1/1972 | Nagel et al. | 62/23 X |
| 3,929,438 | 12/1975 | Harper et al. | 62/11 X |
| 4,002,042 | 1/1977 | Pryor et al. | 62/28 |
| 4,149,864 | 4/1979 | Eakman et al. | 62/11 |
| 4,270,940 | 6/1981 | Rowles et al. | 62/28 |
| 4,272,269 | 6/1981 | Hammond et al. | 62/38 X |
| 4,272,270 | 6/1981 | Higgins | 62/38 X |
| 4,303,427 | 12/1981 | Krieger | 62/23 X |
| 4,356,014 | 10/1982 | Higgins | 62/28 |
| 4,401,450 | 8/1983 | Schramm | 62/28 X |
| 4,410,342 | 10/1983 | Horton | 62/23 |
| 4,443,238 | 4/1984 | Beddome | 62/17 |
| 4,456,460 | 6/1984 | Apffel | 62/28 X |
| 4,461,634 | 7/1984 | Duckett et al. | 62/11 |
| 4,482,369 | 11/1984 | Carson et al. | 62/23 X |
| 4,496,380 | 1/1985 | Harryman | 62/24 |
| 4,507,133 | 3/1985 | Khan et al. | 62/29 |
| 4,519,825 | 5/1985 | Bernhard et al. | 62/28 |
| 4,526,596 | 6/1985 | Baggio et al. | 62/40 |

FOREIGN PATENT DOCUMENTS 2146751A 4/1985 United Kingdom .

OTHER PUBLICATIONS

D. H. MacKenzie and S. T. Donnelly, "Mixed Refrigerants Proven Efficient in Natural Gas Liquids Recovery Process", Oil & Gas Journal, Mar. 4, 1985, pp. 116–120.

T. R. Tomlinson and R. Banks, "LPG Extraction Process Cuts Energy Needs", Oil & Gas Journal, Jul. 15, 1985, pp. 81–84.

Primary Examiner—Albert J. Makay
Assistant Examiner—Steven E. Warner
Attorney, Agent, or Firm—Geoffrey L. Chase; James C. Simmons; William F. Marsh

[57] ABSTRACT

A low temperature phase separation, dephlegmation and distillation process is described for resolving a light hydrocarbon gas stream to recover and purify $C_{3+}$ and/or $C_{4+}$ hydrocarbons. The phase separation bottoms stream is segregated from the dephlegmation bottoms stream and both streams are expanded to produce refrigeration for the feed stream. Both streams are then separately introduced into a distillation column for final purification of the heavy hydrocarbon product.

6 Claims, 6 Drawing Figures

PROCESS FOR RECOVERY AND PURIFICATION OF $C_3$-$C_{4+}$ HYDROCARBONS USING SEGREGATED PHASE SEPARATION AND DEPHLEGMATION

TECHNICAL FIELD

The present invention is directed to the resolution of light hydrocarbon containing streams using low temperature phase separation and dephlegmation. More specifically, the present invention is directed to the recovery and purification of $C_{3+}$ or $C_{4+}$ hydrocarbons from a light gas and light hydrocarbon containing stream using sequential steps of cooling, phase separation, dephlegmation and rectification.

BACKGROUND OF THE PRIOR ART

It is known in the prior art to resolve various light gas streams containing hydrocarbons into a purified light gas stream as one product of the resolution and a heavier hydrocarbon stream such as a $C_2$, $C_3$, $C_{4+}$ or combinations thereof as another product of the resolution. It is also known in the prior art to perfect this resolution with various combinations of low temperature separatory process steps including phase separation, rectification and the use of refluxing heat exchangers sometimes referred to as dephlegmators. It is specifically known to use a combination of low temperature cooling of a feed gas stream followed by phase separation and subsequent dephlegmation to resolve a light gas stream and a heavy hydrocarbon stream from the feed. The heavy hydrocarbon stream can be further resolved in a separatory column.

For example, in UK published patent application GB No. 2146751A published Apr. 24, 1985, to Tomlinson and Cummings, the recovery of LPG or NGL and sales gas from a gaseous hydrocarbon feed is conducted by cooling the feed against process streams and/or refrigeration before phase separating into a light gas and heavy liquid stream followed by dephlegmation of the light gas stream and column stripping of the heavy liquid stream with recycle of the overhead from the column back to feed.

It is also known to perform phase separation and dephlegmation to recover $C_{2+}$ hydrocarbons from a feed gas stream containing light gas components as set forth in U.S. Pat. No. 4,002,042. In that process, feed gas is cooled, phase separated, and the light gas is resolved using dephlegmation with refrigeration from an outside external source and by expanding the light gas stream. The heavy liquid stream from the phase separator is resolved in a rectification column using condenser and reboil duty.

Another prior art teaching of dephlegmation, phase separation and fractionating column processing is set forth in U.S. Pat. No. 4,519,825 wherein $C_{4+}$ hydrocarbons are separated from the feed gas, particularly wherein the dephlegmator operates by refrigeration produced in expanding the light gas product stream to lower temperature and pressure through an expander.

Other prior art having only general relevance to the technology of the present invention wherein analogous feed streams are resolved into light and heavy components by individual or subcombinations of low temperature cooling, phase separation, column separation or dephlegmation are represented in the following art: D. H. MacKenzie and S. T. Donnelly, "Mixed Refrigerants Proven Efficient in Natural Gas Liquids Recovery Process", Oil and Gas Journal Mar. 4, 1985, page 116; T. R. Tomlinson and R. Banks, "LPG Extraction Process Cuts Energy Needs", Oil and Gas Journal July 15, 1985, Page 81; U.S. Pat. Nos. 3,929,438; 4,270,940; 4,272,269; 4,272,270; 4,303,427; 4,356,014; 4,401,450; 4,443,238; 4,456,460; 4,461,634; 4,482,369; 4,507,133 and 4,526,596.

BRIEF SUMMARY OF THE INVENTION

The present invention is a process for the low temperature separation of a feed gas into a heavy hydrocarbon stream containing $C_{3+}$ and/or $C_{4+}$ hydrocarbons and a light gas stream containing $H_2$, $N_2$, CO, $CO_2$, methane and/or $C_2$ hydrocarbons comprising the steps of cooling the feed gas to effect the partial condensation of said gas by indirect heat exchange against process streams, initially phase separating the partially condensed feed gas into a first heavy liquid stream containing heavy hydrocarbons and a first vapor stream containing light gas components, rectifying the first vapor stream by low temperature dephlegmation to produce a first light gas stream and a second heavy liquid stream which is segregated from the first heavy liquid stream, expanding the first and second heavy liquid streams to a lower pressure and temperature and cooling the feed gas with one or both of said streams by indirect heat exchange sufficiently to partially vaporize said stream(s), separately introducing said first and second heavy streams into a distillation column operated with an overhead condenser and a bottom reboiler, separating said streams in said distillation column into a heavy hydrocarbon stream containing $C_{3+}$ and/or $C_{4+}$ hydrocarbons as a bottom product and a second light gas stream and recovering said first light gas stream and second light gas stream to produce one or more product light gas stream(s) containing $H_2$, $N_2$, CO, $CO_2$, methane and/or $C_2$ hydrocarbons.

Preferably, the present invention cools said first vapor stream in the dephlegmator by indirect heat exchange with said first light gas stream which is expanded to a lower temperature and pressure.

Alternatively, the present invention rewarms said first light gas stream by indirect heat exchange against said second light gas stream to provide the reflux duty of said overhead condenser.

Alternatively the present invention utilizes at least a portion of said first or second heavy liquid stream after expansion to a lower temperature and pressure to provide at least a portion of the cooling of said first vapor stream for said dephlegmation or at least a portion of the reflux duty in the overhead condenser of said column, or both.

In another embodiment, the present invention expands the first light gas stream to a lower temperature and pressure in two or more stages through work loaded turbine expanders with interstaged warming in the dephlegmator.

Preferably, the present invention is directed to a process wherein said first heavy liquid stream comprises a predominantly $C_{4+}$ hydrocarbons and said second heavy liquid stream comprises predominantly $C_1$ to $C_3$ hydrocarbons.

Optimally, the present invention is directed to a process wherein the feed gas contains less than 10 mole % $C_{3+}$ hydrocarbons and the recovery of $C_3$ in said heavy hydrocarbon stream is at least 90%.

DETAIL DESCRIPTION OF THE INVENTION

The present invention provides an efficient process for the recovery and purification of $C_{3+}$ and/or $C_{4+}$ hydrocarbons from a light gas stream. Such streams include natural gas streams containing NGL hydrocarbons, and refinery off gases and various petrochemical off gas mixtures containing LPG hydrocarbons. The invention is particularly beneficial to resolution of feed gases containing relatively small amounts of $C_{3+}$ hydrocarbons, for example less than 10 mole % of $C_{3+}$ hydrocarbons, while simultaneously achieving relatively high recoveries of such hydrocarbons, for instance 90% or more of the $C_3$ components and essentially all of the $C_4$ and heavier components in such feed gases. The feed gases can contain any number of light gas components and heavier hydrocarbons. Such light gas components include hydrogen, nitrogen, carbon monoxide and carbon dioxide as well as methane, ethane, and ethylene. The heavier hydrocarbons can include propane, propylene, butane, butene, isobutane, isobutylene, and higher saturated and unsaturated hydrocarbons such as pentane, hexane, and potentially residual amounts of even heavier hydrocarbons. Throughout the text of this patent saturated and unsaturated hydrocarbons are symbolically referenced as propane and propylene equivalent to $C_3$ and butane, isobutane and its butene derivatives identified as $C_4$. The "+" symbol is utilized to indicate the carbon atom count of those hydrocarbon molecular weight compounds and heavier compounds as well represented in the prior art. The present invention is conducted by treating a dry feed gas containing light gases and heavier gases including $C_3$ and heavier hydrocarbons all of which are cooled to an intermediate temperature in the range of 0° to $-50°$ F. to condense initially a $C_{4+}$-rich liquid by phase separation. The remaining vapor is further cooled and rectified in a dephlegmator to recover $C_3$ and residual $C_{4+}$ hydrocarbons. The light $C_3$-rich liquid from the dephlegmator and the heavier $C_{4+}$-rich liquid from the first phase separation are segregated and one or both are rewarmed and partially vaporized before being sent to a distillation column as separate feeds to that column wherein light gases up to $C_2$ hydrocarbons are removed as an overhead while the $C_{3+}$ hydrocarbons are removed as NGL or LPG product. Refrigeration for the dephlegmator is provided primarily by work expansion in one or more stages, preferably with expansion turbines linked to compressors or loads of some sort such as electric generators. If necessary some or all of one or both of the light $C_3$-rich liquid from the dephlegmator or the heavier $C_{4+}$-rich liquid from the separator may be heat exchanged and partially vaporized in the dephlegmator to provide additional refrigeration prior to further vaporization by the initial cooling of feed gas. Refrigeration for the overhead condenser of the distillation column may be provided by external refrigeration, such as a conventional mechanical refrigeration system, or by refrigeration recovery from the light overhead gases from the dephlegmator and/or the distillation column, or by partial vaporization of one or both of the light and heavy liquid streams or other suitable means. Power from the work expansion of the overhead light gas from the dephlegmator may be recovered by compressing the feed gas to the process or by compressing the light gas effluent from the process by a generator or by other suitable linkage means from the turbine expander.

The use of a phase separator dephlegmator and integrated distillation column, combined with work expansion of the light components of the feed for low level refrigeration supply and partial vaporization of the segregated light and heavy liquid streams for high level refrigeration result in significant power savings as compared to alternative processes for recovery and purification of $C_{3+}$ liquid hydrocarbons from natural gas or from refinery and/or petrochemical off-gas streams. The relatively warm temperature of the partial condensation step minimizes the quantity of $C_2$ and lighter components which are condensed in the heavy liquid stream. The refluxing action of the dephlegmator minimizes the quantity of $C_2$ and lighter components which are condensed in the light liquid stream, and reduces the quantity of low level refrigeration required to condense the light liquid stream. As a result, the $C_{3+}$ components are typically concentrated from about 3 to 8 mole % in the feed gas to about 40 to 90 mole % in the feeds to the distillation column, which also reduces the energy requirements in the distillation column to remove the residual light components from the heavy hydrocarbon product.

The process of the present invention shows decided improvements in efficiency in recovering $C_{3+}$ hydrocarbons in comparison to a number of processes describing the prior art, as set forth in Table 1 hereinbelow.

TABLE 1

| Process Cycle | Power | $C_3$ Recovery | $C_{4+}$ Recovery |
| --- | --- | --- | --- |
| Invention | — | 90% | 100% |
| MacKenzie, et al. | +34–57% | 79% | 97–99% |
| Invention | — | 96% | 100% |
| U.S. Pat. No. 4,272,270/ U.S. Pat. No. 4,356,014 | * | 75–93% | 99–100% |
| Invention | — | 94% | 100% |
| Tomlinson, et al./GB2146751A | +21% | 94% | 100% |

*This invention embodiment does not require net power for 96% $C_3$ recovery. The patent cycle doesn't require net power for 75% $C_3$ recovery but requires 170 HP for 93% $C_3$ recovery.

Figure 1:
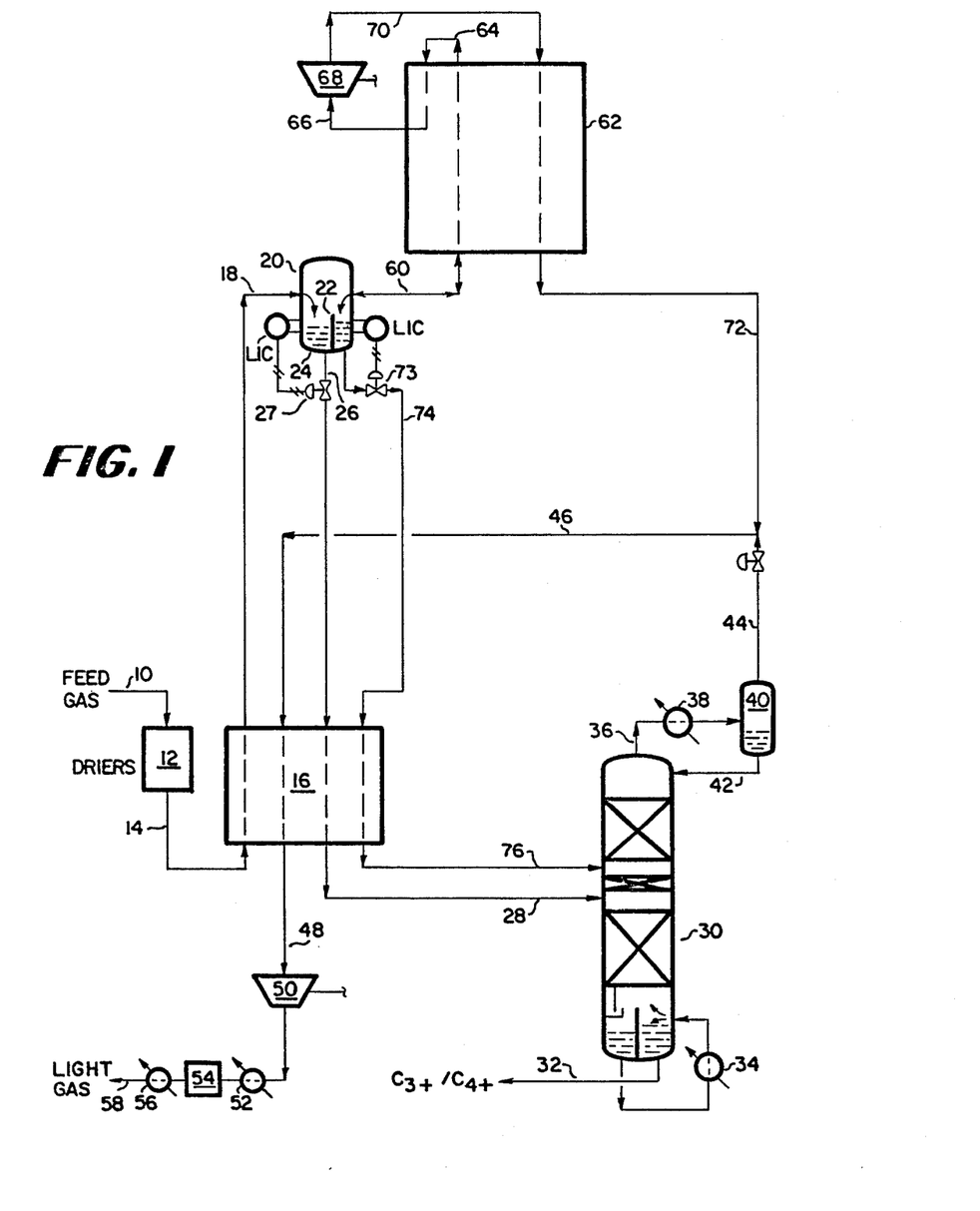
FIG. 1 is a schematic flow scheme of an embodiment of the present invention.

The present invention will further be described with reference to FIG. 1 and a preferred embodiment of the operation of the present invention. A feed gas containing 90% methane, 6% ethane, 2% propane, 1% butane and residual nitrogen, pentanes and hexane is introduced in line 10 at a pressure of 550 psia into a drier 12, where water and condensables are removed. The dried feed gas is then passed through line 14 at 535 psia and 100° F. into a feed cooler 16, comprising a first heat exchanger, wherein the feed gas is cooled against process streams. The feed gas at 530 psia and −30° F. is introduced in two-phase flow in line 18, into a phase separator vessel 20, wherein a significant portion of the $C_{4+}$ hydrocarbons are separated out as a bottom liquid phase, while a predominant amount of the $C_3$-containing gas components remain in the vapor phase. The $C_{4+}$ hydrocarbons remain on the left side of a baffle 22 which divides the phase separator vessel 20 in its lower most liquid containing regions, while the baffle does not separate the overhead or vapor region of the vessel 20. The $C_{4+}$ liquids 24 are removed in line 26 and reduced in temperature and pressure through expansion valve 27 to a temperature of −39° F. and 370 psia. The stream is rewarmed in feed cooler 16 and is then fed as stream 28 at 42° F. and 367 psia as a separate feed into the distillation column 30.

The vapor phase of the feed to the phase separator vessel 20, ascends a dephlegmator heat exchanger 62 in line 60, wherein flow and temperature conditions in the dephlegmator 62 are such that condensible liquids condense out on the heat exchange passageways of the dephlegmator and start to descend such passageways so as to set up reflux or rectifying conditions in the heat exchanger passageways, while the noncondensible light gas components, typically lower molecular weight than $C_3$ hydrocarbons, are removed as a vapor in line 64 and are rewarmed in the dephlegmator-heat exchanger before being supplied in line 66 to a turbine expander 68 to reduce the temperature and pressure of this light gas stream to 336 psia and −117° F. in line 70. This stream then provides refrigeration for the dephlegmator heat exchanger 62 before the gas in line 72 is combined with overhead from the distillation column 30 and removed as a combined gas stream in line 46 and rewarmed in the feed cooler 16. The gas then in line 48 is compressed to 380 psia in compressor 50 which can be preferably powered by the expander 68, either by direct drive or by an electric powered generator attached to the expander and the resulting gas stream can then be aftercooled in aftercooling exchanger 52, further compressed through any series of equipment identified as box 54, aftercooled in aftercooling heat exchanger 56 and removed as a light gas stream product in line 58 at 520 psia and a temperature of 110° F. The product has a composition of 93.7% methane, 6% ethane and 0.2% propane.

Figure 2:
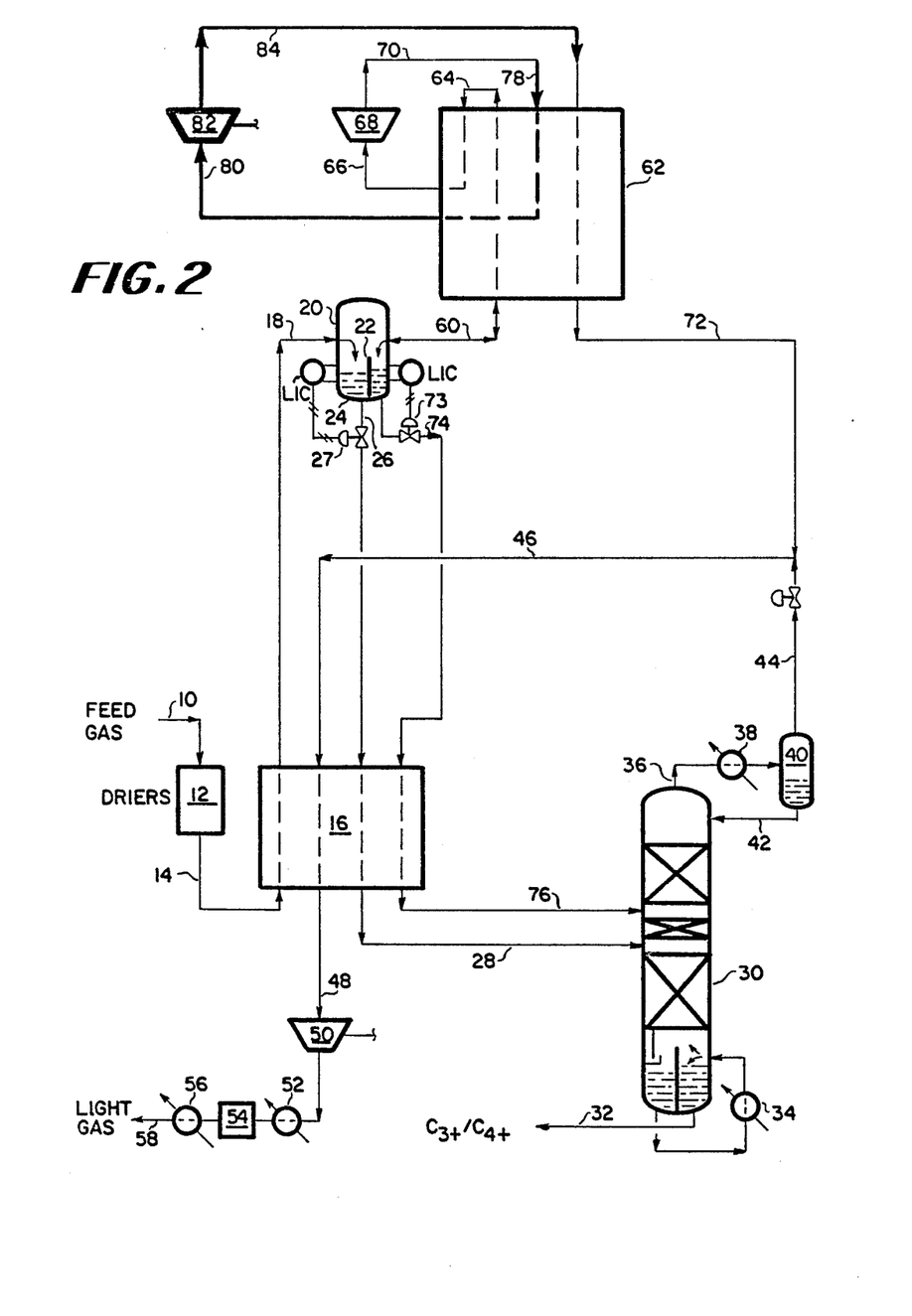
FIG. 2 is an alternate embodiment of the flow scheme of the present invention with the alternate feature shown in heavy line.

The stream in line 70 may be further reduced in temperature and pressure by the alternative flow scheme shown in FIG. 2 line 78, wherein the stream is further rewarmed and taken in line 80 for additional expansion in turbine expander 82 before being further rewarmed by providing refrigeration in the dephlegmator 62 in line 84.

The $C_{3+}$ hydrocarbons, which condense and descend the heat exchange passageways of the dephlegmator 62, return in line 60 to the phase separator vessel 20 on the right-hand side of the baffle 22 and collect as a liquid in that vessel 20 for removal in line 74. This liquid is expanded to a reduced temperature and pressure through expansion valve 73, wherein it achieves a pressure of 370 psia and a temperature of −66° F. This stream then provides refrigeration in feed cooler 16 by rewarming against the incoming feed gas. The stream in line 76 at 367 psia and 42° F. is then introduced above stream 28 as feed to the distillation column 30, whereby the separate introduction to the column 30 of the $C_{3+}$ stream in line 76 and the $C_{4+}$ stream in line 28 provide increased efficiency in the rectification process of that column 30. Light gases that are contained in the feeds in lines 28 and 76 ascend the column as a vapor phase, while the $C_{3+}$ and $C_{4+}$ hydrocarbons in such streams 76 and 28 descend the column and are removed as NGL product in line 32. A certain portion of the product is returned as reboil vapor through the reboil heat exchanger 34. The NGL's comprise predominantly propane with lesser amounts of butane pentane and higher hydrocarbons as well as the un saturated or branched derivatives of such compounds.

Figure 4:
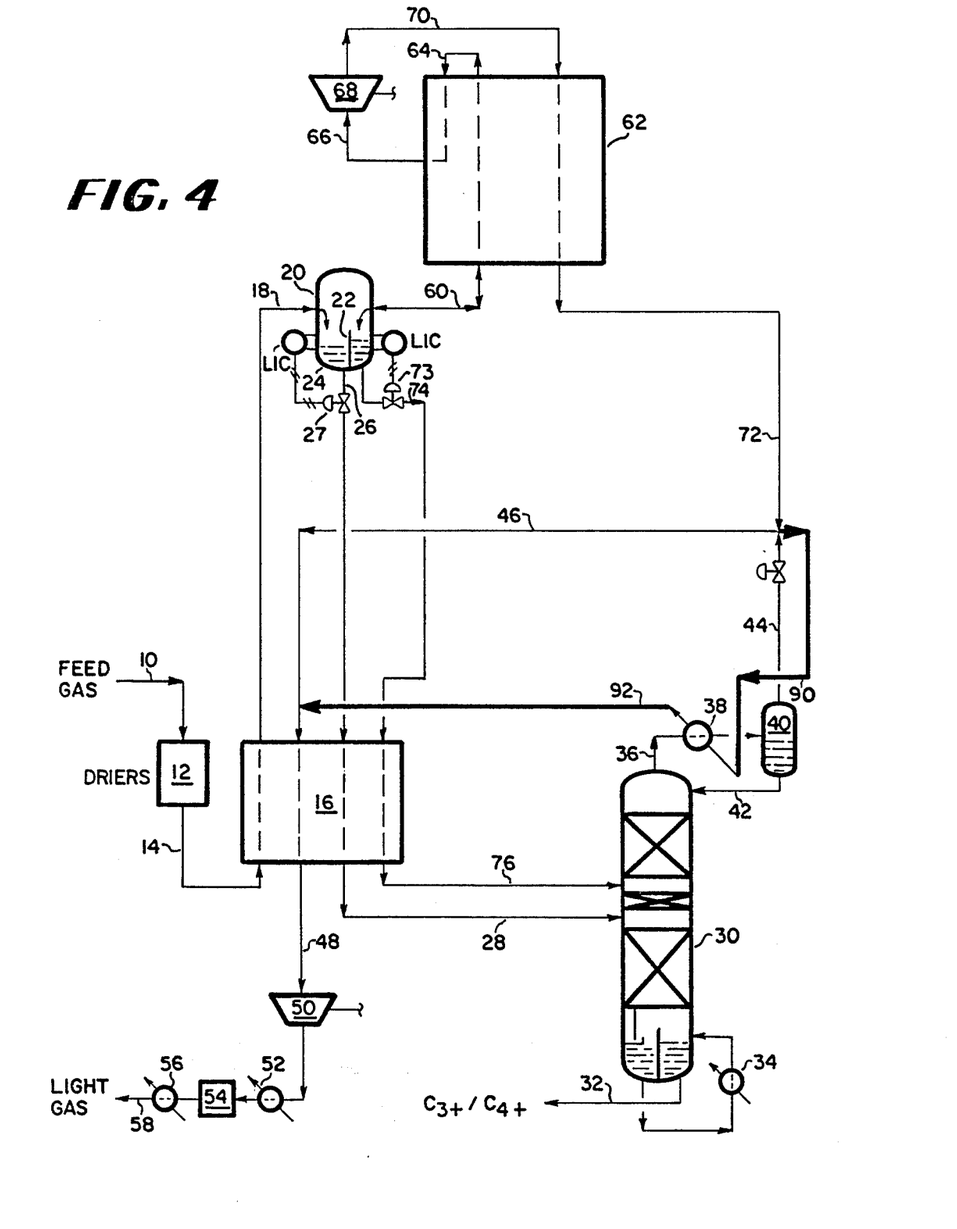
FIG. 4 is an alternate embodiment of the flow scheme of the present invention with the alternate feature shown in heavy line.
Figure 5:
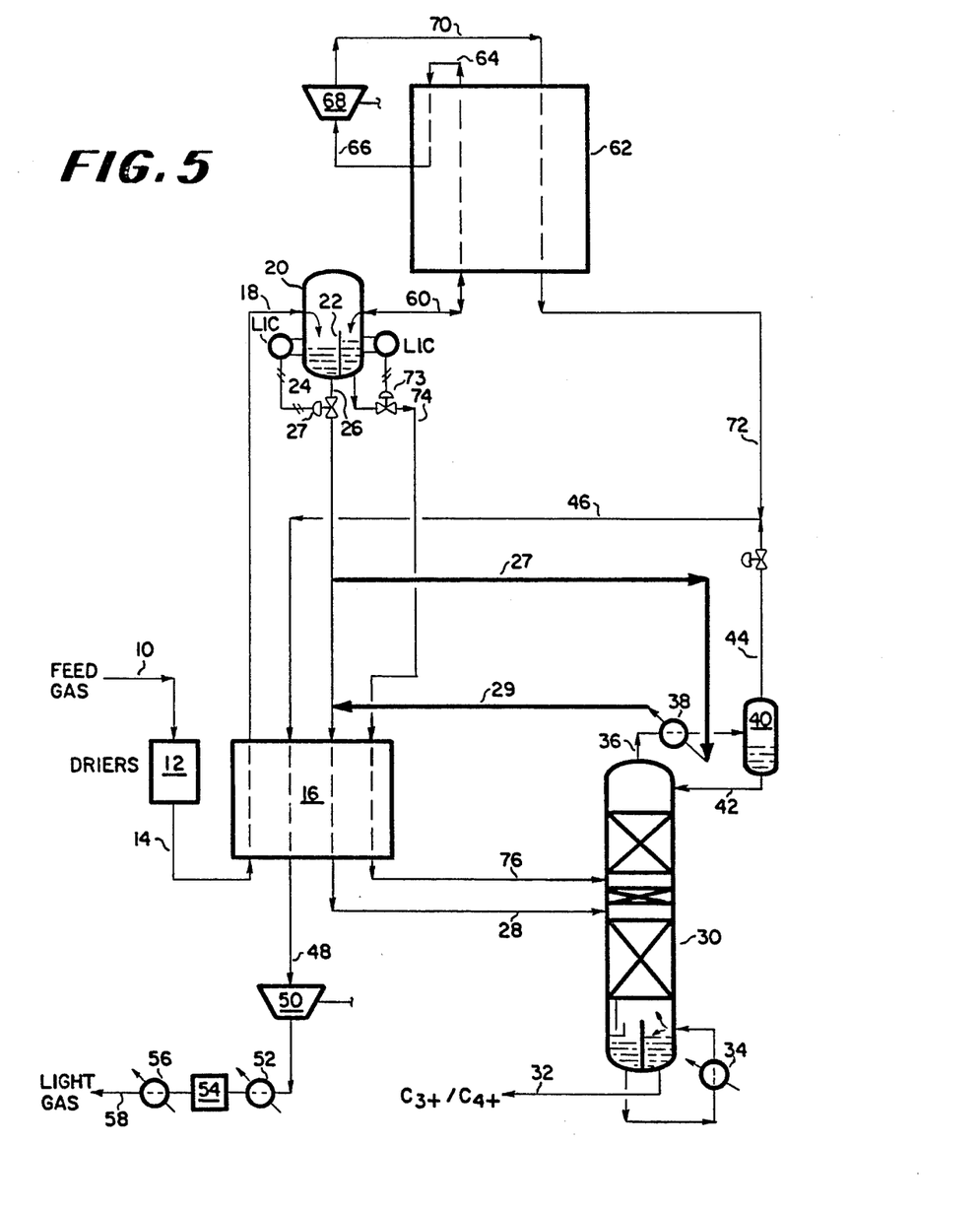
FIG. 5 is an alternate embodiment of the flow scheme of the present invention with the alternate feature shown in heavy line.
Figure 6:
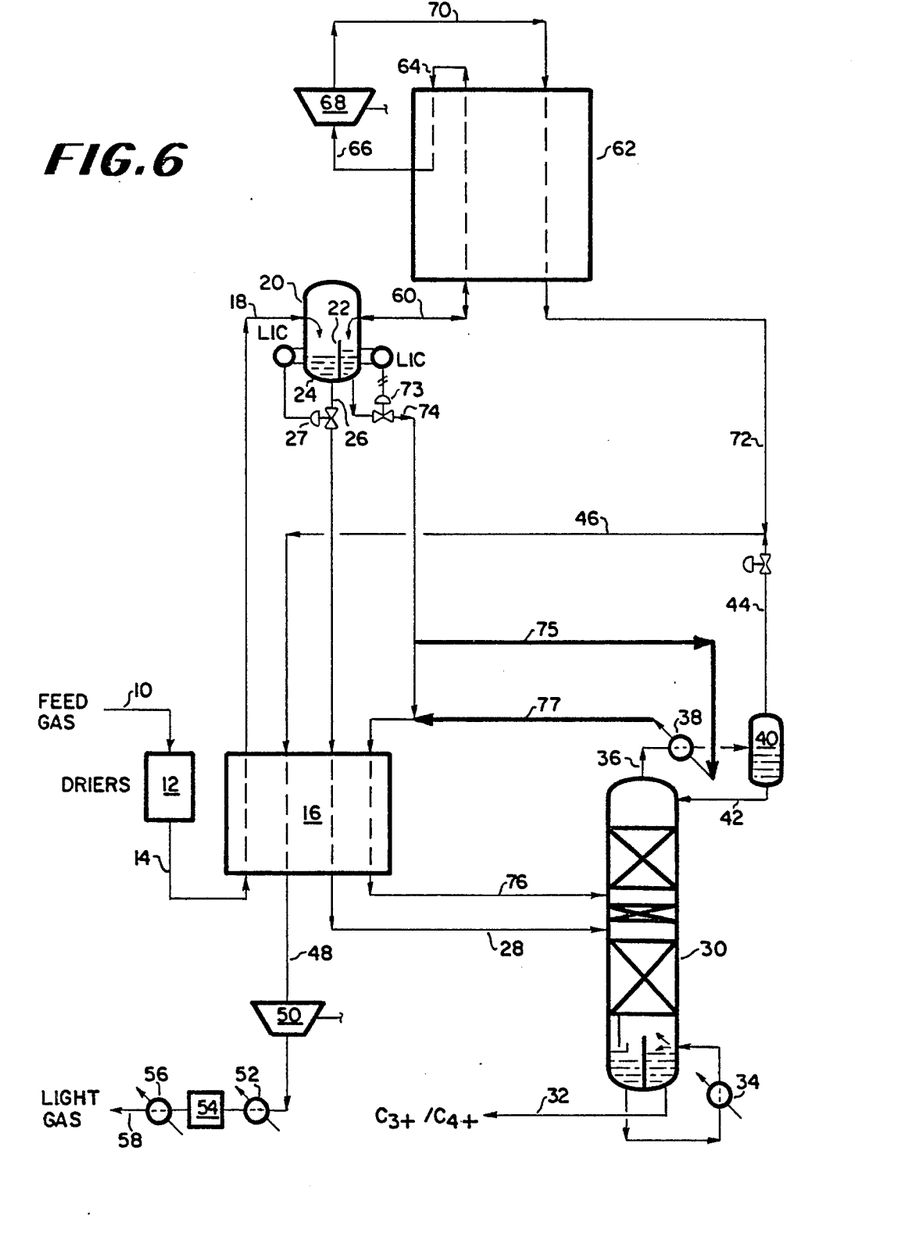
FIG. 6 is an alternate embodiment of the present invention with the alternate feature shown in heavy line.

The light gases in the distillation column 30 are removed in line 36 and cooled in overhead condenser 38 to provide a reflux liquid in phase separation vessel 40, which is returned in line 42 for reflux duty to the column. The vapor phase from the vessel 40 is removed in line 44 and is combined with the stream previously derived from the dephlegmator in line 72. The condensing duty in heat exchanger 38 can be derived from any type of external refrigeration, although alternatively in FIG. 4 it can be supplied by the light gas from line 46 which is removed in line 90, passes through the heat exchanger 38 and is returned in line 92 to stream 46. Alternatively in FIG. 5, reflux duty for the overhead condenser 38 can be derived at least in part from line 26 by removing a stream in line 27, passing it through condenser 38 and line 92 and returning it through line 29 to line 26. In FIG. 6, the same process can be performed with the stream in line 74 by removing a stream in line 75, passing it through condenser 38 and returning it to line 74 through line 77.

Figure 3:
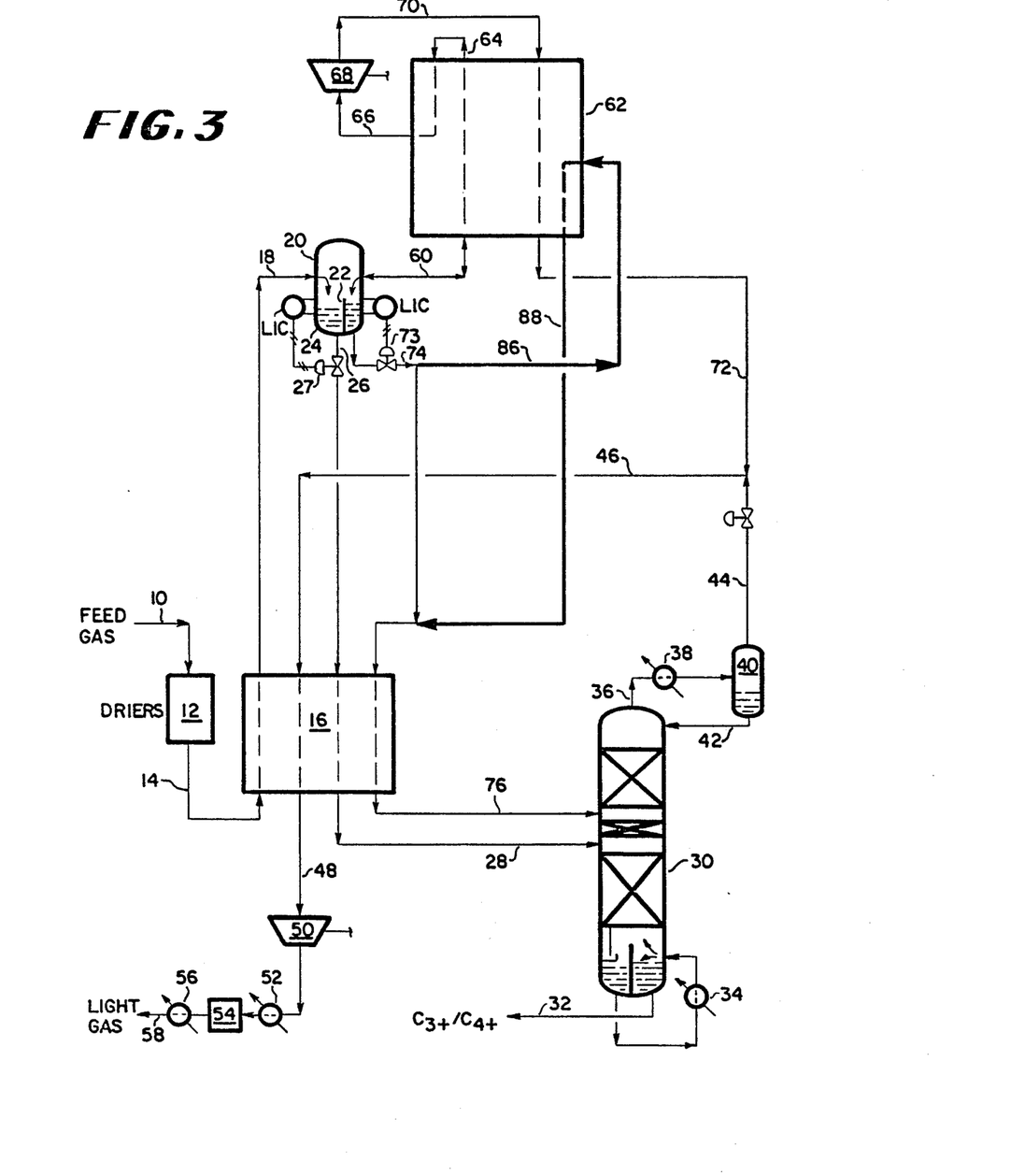
FIG. 3 is an alternate embodiment of the flow scheme of the present invention with the alternate feature shown in heavy line.

The light gas stream 72 from the dephlegmator and the light gas stream 44 from the distillation column could be recovered as separate light gas product streams. In FIG. 3, at least a portion of the stream in line 74 may be diverted through line 86 and rewarmed in dephlegmator or refluxing heat exchanger 62 before being recovered in line 88 and returned to line 74.

The process of the present invention, although similar to various prior art dephlegmator cycles, such as U.K. Patent Application G.B. No. 2146751A, provides several advantages over such processes, including the fact that in that prior art process liquids condensed in the feed cooler and dephlegmator are combined, pumped to feed gas pressure and rewarmed without significant vaporization and fed to the top of the distillation column, which results in an additional refrigeration requirement for feed cooling and additional reboiling duty for $C_{3+}$ purification in the column. In the process of the present invention, the two liquids of the feed cooler and the dephlegmator comprising the $C_{4+}$ and the $C_3$-rich liquid streams, are both separately reduced in pressure and partially vaporized to provide efficient refrigeration for feed cooling, before being separately sent to the distillation column under optimal vapor-liquid feed split conditions for the column as a result of the partial vaporization for refrigeration duty. This supplies the feed in a most efficient manner for operation of the column. The two liquid streams are rewarmed and partially vaporized separately since the lighter $C_3$-rich liquid boils at lower temperatures than the heavier $C_4$-rich liquid. If the two liquids were combined prior to partial vaporization, the resulting mixture would have to be reduced to a lower pressure to provide the necessary refrigeration provided by these streams. This would lower the pressure of the distillation column, and require colder refrigeration for the overhead condenser resulting in a less efficient process.

The prior art process also utilizes its column in a stripping mode without a condenser or rectification duty. This results in uneconomically low $C_{3+}$ recovery, unless the overhead vapor from the column is recycled back to the feed as is shown in that process. However, this recycle flow also results in additional refrigeration requirements for the first feed cooler and the second dephlegmator heat exchanger, particularly requiring additional low level refrigeration in the dephlegmator. Recycling is inefficient because it necessitates final $C_{3+}$ recovery in the purification step from the same very dilute $C_{3+}$ stream as in the initial recovery step. The process of the present invention operates its distillation column with both a stripping and rectification section. The overhead condenser of the column achieves high $C_{3+}$ recovery at relatively warm temperature levels, because the quantity of light gas components in the column is typically less than 5% of the lights in the feed gas. This provides a much more efficient purification step than stripping with recycling of the overhead vapor as in the prior art cycle cited above.

The present invention has been compared to various other dephlegmator lower hydrocarbon separatory processes, as set forth in Table 1, and shows remarkably less power consumption or higher product pressures or higher recoveries or combinations of such advantages. For these reasons, it is believed that the present process has decided and unexpected advantages in the configuration of its process cycle over that of the prior art systems.

The present invention has been set forth with regard to a specific preferred embodiment, but the scope of the invention should be ascertained from the claims which follow.

I claim:

1. A process for the low temperature separation of a feed gas into a heavy hydrocarbon stream containing $C_{3+}$ and/or $C_{4+}$ hydrocarbons and a light gas stream containing $H_2$, $N_2$, CO, $CO_2$, methane, and/or $C_2$ hydrocarbons comprising the steps of:
   (a) cooling the feed gas to effect the partial condensation of said gas by indirect heat exchange against process streams;
   (b) initially phase separating the partially condensed feed gas into a first heavy liquid stream containing heavy hydrocarbons and a first vapor stream containing light feed gas components;
   (c) rectifying the first vapor stream by low temperature dephlegmation to produce a first light gas stream and a second heavy liquid stream which is segregated from the first heavy liquid stream wherein said first vapor stream is cooled in the dephlegmation by indirect heat exchange with said first light gas stream which is expanded to a lower temperature and pressure;
   (d) expanding the first and second heavy liquid streams to a lower pressure and temperature and cooling the feed gas with one or both of said streams by indirect heat exchange sufficiently to partially vaporize said stream(s) as process streams of step (a);
   (e) separately introducing said first and second heavy streams into a distillation column operated with an overhead condenser and a bottom reboiler;
   (f) separating said streams in said distillation column into a heavy hydrocarbon stream $C_{3+}$ and/or $C_{4+}$ hydrocarbons as a bottom product and a second light gas stream; and
   (g) recovering said first light gas stream and said second light gas stream to produce one or more product light gas stream(s) containing $H_2$, $N_2$, CO, $CO_2$, methane, and/or $C_2$ hydrocarbons.

2. The process of claim 1 wherein one or both of said product light gas stream is compressed to elevated pressure after cooling the feed gas stream in step (d).

3. The process of claim 1 wherein said first heavy liquid stream comprises predominantly $C_{4+}$ hydrocarbons and said second heavy liquid stream comprises predominantly $C_1$ to $C_3$ hydrocarbons.

4. The process of claim 1 wherein the recovery of $C_3$ hydrocarbons from the feed gas in the heavy hydrocarbon stream is at least 90%.

5. The process of claim 1 wherein the feed gas contains less than 10 mole % $C_{3+}$ hydrocarbons and the recovery of $C_3$ in said heavy hydrocarbon stream is at least 90%.

6. A process for the low temperature separation of a feed gas into a heavy hydrocarbon stream containing $C_{3+}$, and/or $C_{4+}$ hydrocarbons and a light gas stream containing $H_2$, $N_2$, CO, $CO_2$, methane, and/or $C_2$ hydrocarbons comprising the steps of:
   (a) cooling the feed gas to effect the partial condensation of said gas by indirect heat exchange against process streams;
   (b) initially phase separating the partially condensed feed gas into a first heavy liquid stream containing heavy hydrocarbons and a first vapor stream containing light feed gas components;
   (c) rectifying the first vapor stream by low temperature dephlegmation to produce a first light gas stream and a second heavy liquid stream which is segregated from the first heavy liquid stream wherein the dephlegmation is performed by cooling the first vapor stream by indirect heat exchange with said first light gas stream which latter stream is expanded to a lower temperature and pressure;
   (d) expanding the first and second heavy liquid streams to a lower pressure and temperature and cooling the feed gas with one or both of said streams by indirect heat exchange sufficiently to partially vaporize said stream(s);
   (e) separately introducing said first and second heavy streams into a distillation column operated with an overhead condenser and a bottom reboiler;
   (f) separating said streams in said distillation column into a heavy hydrocarbon stream containing $C_{3+}$ and/or $C_{4+}$ hydrocarbons as a bottom product and a second light gas stream, wherein said first light gas stream is rewarmed by indirect heat exchange against said second light gas stream to provide the reflux duty of said overhead condenser; and
   (g) recovering said first light gas stream and said second light gas stream to produce one or more product light gas stream(s) containing $H_2$, $N_2$, CO, $CO_2$, methane, and/or $C_2$ hydrocarbons.

* * * * *